(12) United States Patent
Seakins et al.

(10) Patent No.: US 6,918,389 B2
(45) Date of Patent: Jul. 19, 2005

(54) BREATHING ASSISTANCE APPARATUS

(75) Inventors: Paul John Seakins, Auckland (NZ); Malcolm David Smith, Auckland (NZ); Mohammad Thudor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 09/808,567

(22) Filed: Mar. 14, 2001

(65) Prior Publication Data

US 2001/0050080 A1 Dec. 13, 2001

(30) Foreign Application Priority Data

Mar. 21, 2000 (NZ) .................................... 503495

(51) Int. Cl.$^7$ ................................................ H05B 3/00
(52) U.S. Cl. ........................... 128/203.27; 128/203.17; 128/203.26; 128/204.17; 261/129; 261/138; 261/142; 454/339
(58) Field of Search ...................... 128/200.24, 201.13, 128/203.12–204.14, 204.17, 205.12, 206.22, 200.14, 204.18; 261/129, 138, 142; 454/339

(56) References Cited

U.S. PATENT DOCUMENTS

| | | |
|---|---|---|
| 485,127 A | 10/1892 | Lynch |
| 3,584,193 A | 6/1971 | Badertscher |
| 3,695,267 A | 10/1972 | Hirtz et al. |
| 3,766,914 A | 10/1973 | Jacobs |
| 3,914,349 A | 10/1975 | Stipanuk |
| 4,013,122 A | 3/1977 | Long |
| 4,013,742 A | 3/1977 | Lang |
| 4,038,980 A | 8/1977 | Fodor |
| 4,060,576 A | 11/1977 | Grant |
| 4,110,419 A | 8/1978 | Miller |
| 4,172,105 A | 10/1979 | Miller et al. |
| 4,500,480 A | 2/1985 | Cambio, Jr. |
| 4,574,188 A | 3/1986 | Midgley et al. |
| 4,640,804 A | 2/1987 | Mizoguchi |
| 4,676,237 A | 6/1987 | Wood et al. |
| 4,710,887 A * | 12/1987 | Ho ............................. 364/555 |
| 4,722,334 A | 2/1988 | Blackmer et al. |
| 4,753,758 A | 6/1988 | Miller |
| 4,829,998 A * | 5/1989 | Jackson ................. 128/203.12 |
| 4,911,157 A | 3/1990 | Miller |
| 4,911,357 A * | 3/1990 | Kitamura .................... 73/336.5 |
| 4,941,469 A | 7/1990 | Adahan |
| 5,031,612 A * | 7/1991 | Clementi ............... 128/204.14 |

(Continued)

FOREIGN PATENT DOCUMENTS

| | | | | |
|---|---|---|---|---|
| DE | 4034611 | | 5/1992 | |
| DE | 94092311 | | 11/1994 | |
| EP | 0258928 | | 9/1988 | |
| EP | 481459 | | 4/1992 | |
| EP | 0672430 | | 9/1995 | |
| EP | 09234247 | * | 9/1997 | ............ 128/203.26 |
| EP | 0885623 | | 12/1998 | |
| EP | 0 885 623 A2 | * | 12/1998 | ............ 128/203.26 |
| GB | 1167551 | | 10/1969 | |
| JP | 05317428 | | 12/1993 | |
| JP | 08061731 | * | 8/1996 | ............ 128/203.12 |
| JP | 09234247 | * | 9/1997 | ............ 128/203.17 |
| SU | 379270 | | 4/1973 | |
| WO | WO9826826 | | 6/1998 | |
| WO | WO 0110489 | | 2/2001 | |

Primary Examiner—Glenn K. Dawson
(74) Attorney, Agent, or Firm—Trexler, Bushnell, Giangiorgi, Blackstone & Marr, Ltd.

(57) ABSTRACT

A humidifier and humidity sensor for use with a breathing assistance apparatus. The humidity sensor senses absolute humidity, relative humidity and/or temperature at both the patient end and humidifier end. The humidifier may also include provision to both control independently the humidity and temperature of the gases. Further, a chamber manifold facilitates easy connection of the humidifier to various outlets, inlets and sensors. A heated conduit provides a more effective temperature profile along its length.

37 Claims, 4 Drawing Sheets

U.S. PATENT DOCUMENTS

| | | | |
|---|---|---|---|
| 5,062,145 A | | 10/1991 | Zwaan et al. |
| 5,092,326 A | | 3/1992 | Winn et al. |
| 5,101,820 A | | 4/1992 | Christopher |
| 5,148,801 A | * | 9/1992 | Douwens et al. ...... 128/203.16 |
| 5,224,923 A | | 7/1993 | Moffett et al. |
| 5,336,156 A | | 8/1994 | Miller et al. |
| 5,346,128 A | | 9/1994 | Wacker |
| 5,367,604 A | | 11/1994 | Murray |
| 5,388,443 A | * | 2/1995 | Manaka ...................... 73/31.06 |
| 5,392,770 A | | 2/1995 | Clawson et al. |
| 5,404,729 A | | 4/1995 | Matsuoka et al. |
| 5,454,061 A | | 9/1995 | Carlson |
| 5,482,031 A | * | 1/1996 | Lambert ................ 128/203.12 |
| 5,529,060 A | * | 6/1996 | Salmon et al. ......... 128/203.16 |
| 5,558,084 A | * | 9/1996 | Daniell et al. ......... 128/203.17 |
| 5,564,415 A | | 10/1996 | Dobson et al. |
| 5,588,423 A | * | 12/1996 | Smith .................... 128/203.26 |
| 5,640,951 A | * | 6/1997 | Huddart et al. ........ 128/204.17 |
| 5,673,687 A | | 10/1997 | Dobson et al. |
| 5,759,149 A | | 6/1998 | Goldberg et al. |
| 5,769,071 A | | 6/1998 | Turnbull |
| 5,988,164 A | * | 11/1999 | Paluch .................. 128/203.16 |
| 6,024,694 A | | 2/2000 | Goldberg et al. |
| 6,050,260 A | * | 4/2000 | Daniell et al. ......... 128/204.22 |
| 6,078,730 A | | 6/2000 | Huddart et al. |
| 6,095,505 A | * | 8/2000 | Miller ........................ 261/130 |
| 6,125,847 A | * | 10/2000 | Lin ....................... 128/204.17 |
| 6,158,431 A | * | 12/2000 | Poole .................... 128/203.12 |
| 6,311,958 B1 | | 11/2001 | Stanek |
| 6,349,722 B1 | * | 2/2002 | Gradon et al. ......... 128/203.17 |
| 6,367,472 B1 | * | 4/2002 | Koch .................... 128/203.12 |
| 6,394,084 B1 | * | 5/2002 | Nitta ..................... 128/201.13 |
| 6,397,846 B1 | | 6/2002 | Skog et al. |
| 6,463,925 B2 | * | 10/2002 | Nuckols et al. .............. 126/208 |
| 6,474,335 B1 | * | 11/2002 | Lammers ............... 128/205.12 |
| 6,543,412 B2 | | 4/2003 | Amou et al. |
| 6,564,011 B1 | | 5/2003 | Janoff et al. |
| 6,694,974 B1 | | 2/2004 | George-Gradon et al. |
| 2002/0186966 A1 | | 12/2002 | Zimmer et al. |

* cited by examiner

BREATHING ASSISTANCE APPARATUS

BACKGROUND TO THE INVENTION

1. Field of the Invention

The present invention relates to the use of an humidification system particularly, but not solely, for providing respiratory assistance to patients receiving mechanical ventilation or respiratory support.

2. Summary of the Prior Art

A number of methods are known in the art for supplying humidified gases to a patient requiring breathing assistance. Such prior art humidifiers generally comprise a source of pressurised air (or other mixture of gases), a humidification chamber including a source of water and a heating means to vaporise the water, and a conduit to convey the humidified gases to the patient or user.

For example U.S. Pat. No. 4,038,980 describes a "flash vaporisation" humidifier where water drips onto a low thermal mass heater to create respiratory humidity. It mentions "control means may be provided automatically to regulate the water supply rate in response to means sensing the relative humidity", however they prefer a manual control of water flow rate. Thus it incorporates a humidity sensor and controls the water rate, as opposed to controlling the amount of electrical heating.

U.S. Pat. No. 5,092,326 also describes the use of a humidity sensor in a humidifier. It describes a high frequency ventilation system that incorporates a heated humidifier and a humidity sensor, where these are linked to a central microprocessor. Apparat us is disclosed to moisten a gas mixture supplied to the airway, and a microprocessor controls the amount of moisture supplied to the gas mixture. While it discloses a humidity sensor at the patient airway, it doesn't describe the actual humidification configuration to be used.

U.S. Pat. No. 5,769,071 describes a humidifier incorporating a heat and moisture exchanger (HME), supply of water to the HME, heater element and humidity sensor. The humidity sensor can control humidity via water supply rate or temperature (via the heater element). Also the humidity sensor is described as being at the patient airway.

U.S. Pat. No. 5,988,164 describes a heated breathing tube system for use with a humidifier. This uses a relative humidity sensor (located near the patient) to control the amount of heating provided by the heated breathing circuit so that the gas is at a constant level of relative humidity. The heated breathing circuit may use either electrical heating, or heating via warm recirculating water in a tube. Also described is a method of control of the electric heater wire or heated water tube based on the output of relative humidity sensor.

The previously mentioned U.S. Pat. Nos. 4,038,980 and 5,769,071 both describe humidifiers where the humidification chamber is located close (proximal) to the patient. These have the disadvantage of introducing weight, heat and complexity near the patient which is inconvenient and could be painful to the patient. Of the cited prior art only U.S. Pat. No. 5,988,164 specifically describes the humidification chamber as being located remotely from the patient.

There are several disadvantages of the prior art systems using a humidification chamber located remotely from the patient. It is normally assumed that gases leaving such prior art humidifiers are saturated with water vapour (100% relative humidity). However there is no guarantee that the gases leaving such humidifiers are in fact saturated with water vapour. In certain circumstances (e.g. with the incoming air already warm), the gases leaving such humidifiers can be significantly less than 100% relative humidity. This is because as they are typically controlled to achieve a desired outlet gas temperature, which in such cases may not be much more than the incoming air.

Another drawback of the prior art systems is that condensation can occur in the (sometimes heated) conduits connecting the patient to the respiratory assistance equipment. This may occur if the temperature profile along such conduits is not even and allows some parts of the conduit to be colder than the gas at these points.

A third disadvantage of such prior art systems is where the gas leaving the humidifier is at 100% relative humidity it must be heated immediately by some form of conduit heater or it may lose heat through the walls of the conduit, which results in condensation and therefore a drop in the amount of absolute humidity contained in the gas.

Another fourth disadvantage of the prior art systems is the need for a sensor very near to the patient, which adds to the weight and bulk of equipment at the patient's airway.

A fifth disadvantage of the prior art systems is that intermittent or varying flow rates will cause the absolute humidity that is generated by the humidifier to be uneven. This is because the flow rate is varying faster than any control loop that might operate in such humidifiers. Air which passes through the humidifier at a high flow rate has had little time to be heated and humidified, while air that passes through the chamber at a low flow rate will be hotter and contain higher absolute humidity. Consequently it is difficult for a conduit in such prior art systems to transport these high humidity boluses without condensation and consequent loss of absolute humidity.

SUMMARY OF THE INVENTION

It is therefore an object of the present invention to provide a humidification system which goes some way to overcoming the above mentioned disadvantages, or which will at least provide the public with a useful choice.

Accordingly in a first aspect the present invention consists in a humidification apparatus for humidifying a gases flow to be supplied to a patient or other person in need of such gases comprising:

humidification chamber means and having an inlet and an outlet to allow said gases flow to pass through said humidification chamber means, chamber heating means provided adjacent said humidification chamber means and adapted to vaporise liquid water in said humidification chamber means in order to provide water vapour to said gases flow passing through said humidification chamber means, gases transportation pathway means connected to said outlet of said humidification chamber means to convey said gases flow to said patient or other person in need of such gases, and humidity sensing means configured to provide an indication of the absolute humidity of said gases flow at least at one point in the flow path through said apparatus of said gases flow.

In a second aspect the present invention consists in a humidification apparatus for humidifying a gases flow to be supplied to a patient or other person in need of such gases comprising:

a humidification chamber and having an inlet and an outlet to allow said gases flow to pass through said humidification chamber, chamber heater provided adjacent said humidification chamber adapted to vaporise liquid water in said humidification chamber in order to provide water vapour to said gases flow passing through said humidification chamber, a conduit connected to said outlet of said humidification chamber to convey said gases flow to said patient or other person in need of such gases, and a regulated conduit heater adapted to regulate the temperature profile of said gases flow along said conduit and/or of said conduit, to substantially coincide with a predetermined profile.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 1:
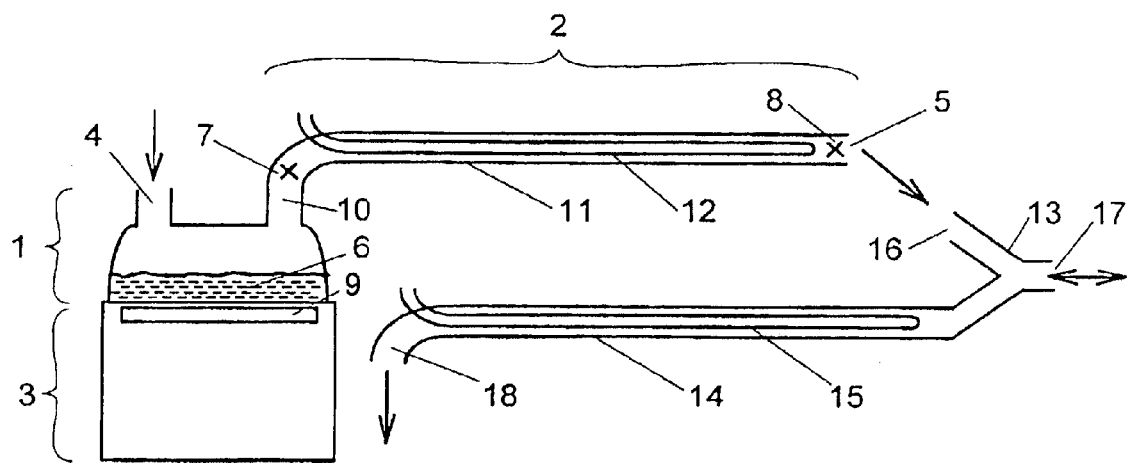
FIG. 1 shows an example of an humidification system, comprised of three parts.

FIG. 1 illustrates a typical respiratory humidification system, comprised of three parts:
1) a humidification chamber located at a distance from the patient, which heats and substantially saturates gases flowing through it;
2) a delivery system consisting of a flexible tube which carries humidified gases from the humidification chamber 1 to the gas outlet 5; and
3) a heater base 3 which heats the humidification chamber 1 and provides measurement and control functions.

The gas to be humidified flows into the chamber 1 from port 4 and leaves the delivery system 2 at gas exit port 5. Gas from exit port 5 flows to a patient via a face mask or similar (not shown). The system is controlled using sensors located at positions 7 and 8—typically temperature probes. Dry gases at the gas input 4 are heated and humidified by passing over the surface of hot water 6 in the chamber 1 so that they are substantially saturated with water vapour when they leave chamber 1 at exit port 10. Hot water 6 is heated by heater plate 9 and the amount of heating is controlled so that the gas reaches a predetermined temperature at exit port 10. This temperature is measured by sensor 7. Therefore the humidification chamber 1 acts to heat and humidify the medical gases so that they are substantially saturated at the output of chamber 1, and are at a predetermined temperature.

The gas delivery system 2 (also known as a delivery tube or breathing circuit) consists of a flexible tube 11 containing a heater 12, which may consist of a heated resistance wire. The gas from the humidification chamber 1 passes through the tube 11 and is heated by heater 12 to offset heat losses through the walls of tube 11. The amount of heating applied to heater 12 is regulated so that the gas reaches a predetermined temperature at gas outlet 5, as measured by sensor 8. The control temperature at sensor 8 is usually higher than the control temperature at sensor 7, so that the gas is heated along tube 11 to ensure that condensation doesn't occur in the tube.

The system as described has gas entering gas inlet 4 from a continuous flow gas source (not shown) and exiting the system through gas outlet 5. However the system is equally applicable where the gas source is a ventilator, which creates intermittent flow patterns to provide breaths to a patient. In this case gas outlet port S is connected directly to gas inlet port 16. The patient is connected to port 17 via an endotracheal tube or similar (not shown). During patient inspiration dry gases from the ventilator enter the system at inlet port 4, pass through chamber 1, delivery system 2, pass through wye-piece 13 and reach the patient through port 17. During patient exhalation gases pass back through port 17, through wye-piece 13, tube 14 and leave through gas outlet port 18. Tube 14 may also be heated by heater 15 to prevent condensation.

Absolute Humidity Sensing

Humidifiers incorporating humidity sensors for display or control have been described in the prior art, however all used humidity sensors which were positioned at the patient airway. The current work describes novel humidifier configurations incorporating a humidity generating chamber located at a position which is remote from the patient, a heated breathing circuit to transfer humidity to the patient and humidity sensors to control the level of absolute or relative humidity supplied to the patient. These humidity sensors are to be located either:
1) at the chamber outlet only,
2) at both the chamber outlet and near the patient, or
3) near the patient only.

One aspect of the present invention would be to use a humidity sensor as sensor 7. The purpose of humidity sensor 7 is to determine the absolute amount of humidity which is being generated by chamber 1. Accordingly an absolute humidity sensor would be ideal for use as sensor 7, although the use of a relative humidity sensor with associated temperature sensor could equally be used This system has the advantage of creating a controlled level of absolute humidity at chamber outlet 10, however this level of absolute humidity may not reach the patient if condensation is allowed to occur in tube 11.

An alternative system which would overcome this disadvantage is to use a second absolute humidity sensor at point 8 instead of a temperature sensor. The difference in absolute humidity between sensors 7 and 8 allows the humidifier to determine whether condensation is occurring between the two points. If the two absolute humidity sensors 7 and 8 read the same level of absolute humidity then no condensation is occurring in the tube. If the absolute humidity at sensor 7 is greater than at sensor 8, then the difference shows the rate of condensation that is occurring.

One control strategy would be to control the amount of heating provided to heater 12 so that the absolute humidity difference is reduced to zero. However the tube may still contain mobile condensate because the humidity difference only describes the rate of condensation, not the absolute amount of condensate in the tube. Another control strategy is to remove this condensate and hence create a dry tube by heating heater 12 so that the rate of measured condensation is negative (i.e. condensation is being evaporated in tube 11) until the measured condensation rate reaches zero, indicating that all of the condensate has been removed. The amount of heating can then be reduced until the sensors show that condensation has just started to occur, then the heating can be increased slightly to the optimum level. Drying out of the tube may be a continuous process, or may be initiated at regular time intervals.

Another variation of the system shown in FIG. 1 would be to use a temperature sensor for sensor 7 and an absolute humidity sensor at point 8. This system is simpler than having an absolute humidity at both points 7 and 8. In operation the controller would have to adjust the amount of heating at heater 12 and heater plate 9 so that the correct level of absolute humidity was reached without condensate in delivery tube 12. In practice two separate control algorithms would be required, one to control the amount of heating occurring in tube 11 so that no condensation occurred, and another to control heater plate 9 so that the desired level of absolute humidity was generated in chamber 1. The two algorithms could work concurrently because the heater plate 9 will respond slower than heater 12, so quick changes in absolute humidity would indicate the action of heater 12. Sensor 7 provides a control point for heater plate 9, but may not be needed.

Low Relative Humidity Chambers

All systems described so far have used a chamber 1 which attempts to humidify the gas leaving gas outlet 10 to a high level of relative humidity. While this condition isn't essential for the correct operation of the new humidification configurations just described because they use humidity control, it was essential for the prior art humidifier where control is purely based on temperature. However there are some advantages to be gained from using a chamber which heats gases to the correct absolute humidity, but at a low relative humidity (i.e. the temperature of the gas is higher than the dewpoint of the gas, therefore the gas is not saturated).

The first advantage is that it is easier to design a heated delivery system to transport such a gas without condensation, since the gas doesn't need to be heated immediately after it enters the delivery tube to prevent condensation. Secondly, the use of low relative humidity gases leaving the chamber means that the heater element 12 can be rated at a lower power than would otherwise be the case, as the gas already has a higher energy content and can tolerate a greater loss of energy before the gas condenses in the tube 12. It may even be possible to use an unheated, well insulated breathing circuit instead of a heated breathing circuit if the chamber provides gas with enough energy. Note that low relative humidity chambers can only be used if the heating to the chamber is controlled using an absolute humidity sensor, not a temperature sensor, since otherwise the absolute humidity output would be too low.

Figure 2:
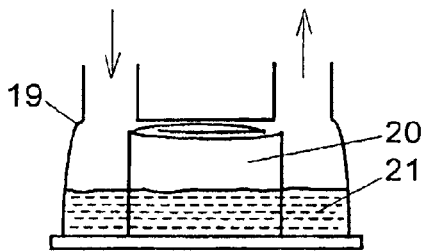
FIG. 2 shows a chamber which incorporates a metal element.

To this end, some humidification chamber configurations which provide a high temperature, low relative humidity gas output are shown in FIGS. 2–8. FIG. 2 shows a chamber which incorporates a metal element 20 (e.g. a spiral scroll shape), but without wicking paper attached. This provides both dry heating (via the metal element) and heated humidification from the heated water 21. With this configuration the chamber 19 provides gas which is not saturated because some of the heating provided to the gas is dry heating via the metal scroll. The relative humidity generated by the chamber is affected by the gas flow path, scroll shape, dimensions, and the water level, and so is not readily adjustable in use. However chamber 19 does give the condensate reducing advantages provided by a low relative humidity, controlled absolute humidity output.

Figure 3:
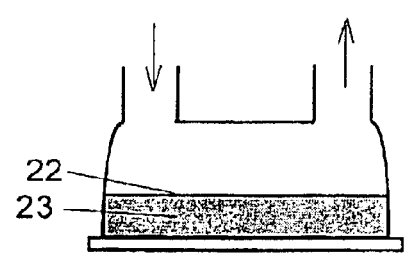
FIG. 3 shows a chamber using a porous material to provide a heating and humidifying function.
Figure 4:
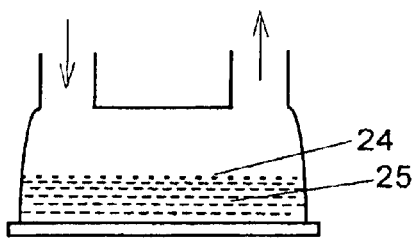
FIG. 4 shows a chamber using a semipermeable membrane.

FIGS. 3 and 4 are alternative humidification chambers which provide low relative humidity, high temperature gases at their output. FIG. 3 shows a chamber using a porous material 22 (such as a porous ceramic) containing water 23 to provide a heating and humidifying function, while FIG. 4 shows a chamber using a semipermeable membrane 24 to provide a barrier to the water 25 in the chamber. In both cases these chambers provide dry heating via the porous or semipermeable material, as well as heated humidification from the water. In both cases the ratio of heating to humidifying is fixed and cannot be easily adjusted except by limiting the water supply.

Figure 5:
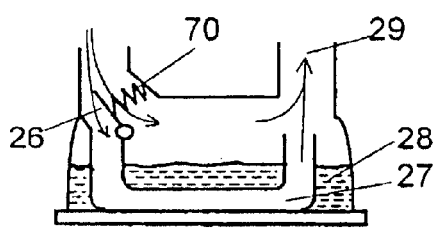
FIG. 5 shows a chamber with a variable valve to adjust the ratio of gas which are bypassed.

FIGS. 5 to 8 show chambers that can supply gases at varying levels of relative humidity and temperature. In FIG. 5 a variable valve 26 allows us to adjust the ratio of gas which passes through the dry bypass tube 27 to that which flows across the surface of the water 28. The bypass tube passes under the water to heat the gas. The two gas streams merge at the output 29. This is an example of a "parallel" system where the gas splits and takes two different paths to provide heating and humidification. In FIG. 6 the gas is again split into two gas paths using an adjustable valve 30. One part of the gas gets humidified by passing across the water 31 in chamber 32, while the other is heated by heater 58, which surrounds tube 33. The gas paths merge at junction 34.

Figure 6:
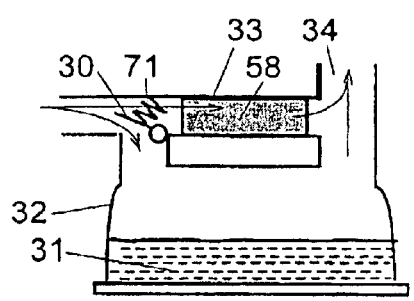
FIG. 6 shows a chamber with an adjustable valve 30 where one part of the gas gets humidified while the other is heated.

The angle of variable valves 26 and 30 in FIGS. 5 and 6 may be permanently set, may be manually adjustable, or may be automatically adjustable. One advantage of an automatically adjustable valve would be to provide a constant level of humidity out of the chamber when used with intermittent flow rates, for example when used with a ventilator. These flow patterns can be a problem because parts of the breath cycle contain less humidity than other parts, due to the chamber providing less humidity at higher Sow rates. One way to overcome this problem is to measure the instantaneous flow rate using a fast response flow sensor, and then rapidly adjusting the angle of the variable valve. A more practical method of achieving this effect would be to spring-load valves 26 and 30 using springs 70 and 71. This would mean that low flow rates would mostly pass through the bypass tubes, while high flow rates would operate the spring-loaded valve and allow more gas to pass across the water in the humidification chamber. The angle of the spring-loaded variable valve could also be used by the humidifier to measure the gas flow rate.

Figure 7:
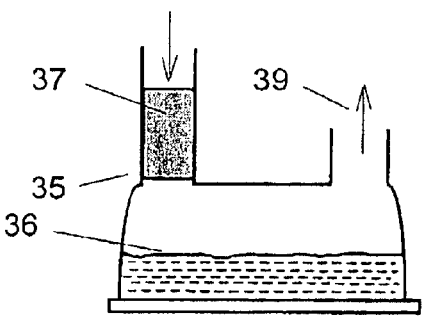
FIG. 7 shows a chamber where the dry gas entering chamber is pre-heated.
Figure 8:
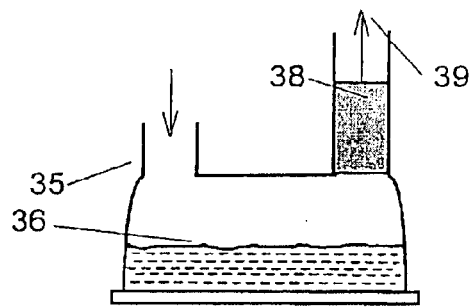
FIG. 8 shows a chamber where the dry gas entering chamber is heated after leaving the chamber.

FIGS. 7 and 8 show alternative series configurations for low relative humidity chambers, where the dry gas entering chamber 35 containing heated water 36 is either pre-heated via heater 37 in FIG. 7, or heated via heater 38 in FIG. 8 after leaving the chamber. In both cases the heater provides dry heating to the gas and results in a low relative humidity, high temperature gas leaving outlet 39.

Any of the low relative humidity, high temperature chambers shown in FIGS. 2 to 8 can be used in conjunction with the humidity control schemes described previously in this patent, but not successfully with the prior art humidifier due to it being temperature controlled, not humidity controlled.

Insulated Delivery Tube

Figure 9:
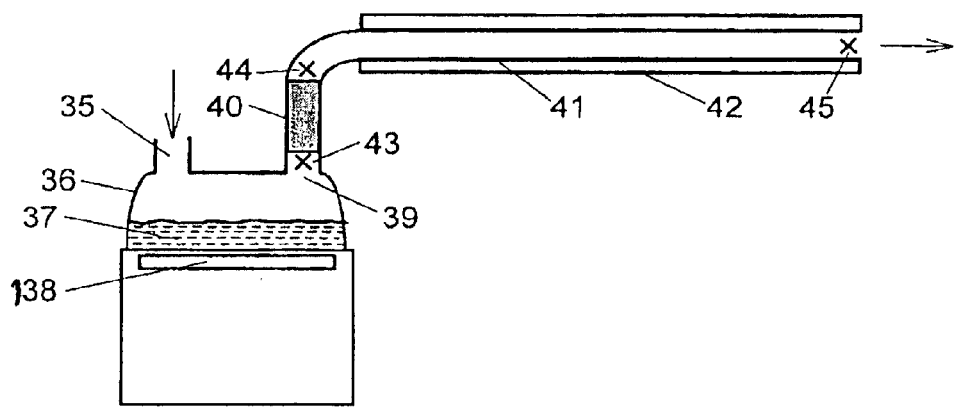
FIG. 9 shows a chamber combined with an unheated, well insulated delivery tube.

Another facet of the invention is shown in FIG. 9. Here the low relative humidity, high temperature humidification system from FIG. 8 has been combined with an unheated, well insulated delivery tube. The incoming gas enters at port 35 into the standard humidification chamber 36 containing water 37 which is heated by heater plate 38. The gas is substantially saturated in the chamber then leaves the chamber through gas outlet 39 and enters heated tube section 40 which heats the humid gas to a higher temperature, so that it has a low relative humidity. The gas then passes through tube 41 which has an insulating layer 42 around it. Preferably the insulating layer is a thin jacket of stagnant air which reduces heat loss. As the high temperature gas, low relative humidity gas passes through the insulating tube, a small amount of heat is lost through the tube walls, and therefore the gas cools. However the amount of heating applied to heater 40 is controlled, so that the gas is never allowed to cool below its dewpoint, which would result in condensation within tube 41.

Several different sensor configurations are proposed. Firstly, sensor 43 could be an absolute humidity sensor which controls heater plate 38 so that chamber 36 produces the desired level of humidity. In one embodiment sensor 45 is a temperature sensor, which controls heater 40 so that the gas passing sensor 45 remains at a certain desired temperature. If this temperature is greater than the dewpoint of the gas at sensor 43, then condensation should not occur in tube 41. However there may already be condensate in tube 41 when the humidifier is turned on. If a humidity sensor is used for sensor 45 instead of a temperature sensor, then the level of condensate occurring in the tube 41 can be controlled. The algorithms described earlier in this patent for dual-humidity sensor control can be used with this system.

An alternative location for the absolute humidity sensor is at position 44 instead of 43. The absolute humidity here should be the same as at 43 because the gas has been heated and so hasn't lost any moisture. However there may be advantages to placing the absolute humidity sensor at 44, for instance due to better sensor operation in a low relative humidity environment. This location for the absolute humidity sensor can be used with either a temperature or absolute humidity sensor at location 45.

Humidifier Configurations Without Any Patient Airway Sensors

Yet another aspect of this patent relates to removing the need for a sensor at the patient airway. To remove this sensor safely, we must be certain that the gas entering the delivery tube has a safe level of temperature and absolute humidity, and that the surfaces inside the delivery tube do not exceed safe temperature levels. This implies a delivery tube that has a constant internal wall temperature.

It would be desirable, therefore, to have a heated delivery tube which self-regulates its temperature at a desired level. The heater could either be embedded in the wall of the delivery tube itself, or it could lie inside the lumen of the delivery tube, or it could be wrapped around the outside of the delivery tube. Such a heater could be made from positive temperature coefficient (PTC) material (such as "Winterguard" from Raychem Corp., Menlo Park, Calif. USA), so that the resistance of the heater increases if The heater is hot, resulting in reduced power. However the delivery tube nay pass through more than one environment, or may have localised drafts present on certain parts of the tube. If the PTC elements are arranged in parallel, then the fill benefit of the PTC heater can be envisaged. If the PTC elements are arranged in parallel, then the cold portions of the tube will have a lower resistance, which will result in more heat being dissipated. Thus the tube will tend to regulate its own temperature.

Figure 10:
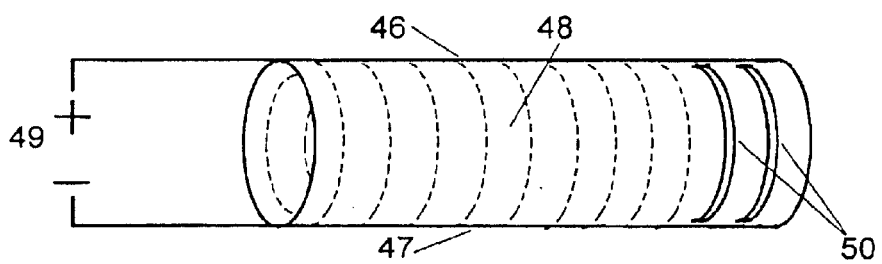
FIG. 10 shows construction of a tube incorporating flexible PTC elements in a parallel wire configuration.

FIG. 10 shows construction of a tube incorporating flexible PTC elements in a parallel wire configuration. The tube 48 is made of a flexible PTC material, which has two low resistive strip connections, 46 and 47, on either side of it. This allows each portion of the tube to consist of short conducting segments of tube connected in parallel between conductors 46 and 47. These segments are represented by dotted lines encircling the tube in FIG. 10. The conductors 46 and 47 are connected to adjustable voltage source 49, which may be AC or DC. The tube would have an outer layer (not shown) which provides electrical insulation and thermal insulation to the tube. Each longitudinal segment of the tube will be able to regulate its own temperature independently of the rest of the tube. To enhance this operation, it may be necessary to provide parallel slots 50 running perpendicular to the axis of the tube, to eliminate electrical cross-connection between the different PTC segments.

Although one specific PTC heated tube design has been envisaged and described, other PTC tube designs could be used. It may also be of advantage to create a PTC tube that has a differing temperature profile along its length rather than a constant temperature profile. The PTC design could also be extended to incorporate PTC heaters in other parts of the patient breathing circuit, such as the flexible extension tube which is usually connected between the Y-piece (port 17 of FIG. 1) and the patient's endotracheal tube. A further extension of the PTC tube concept would be into a self-heated and temperature controlled endotracheal tube.

Figure 11:
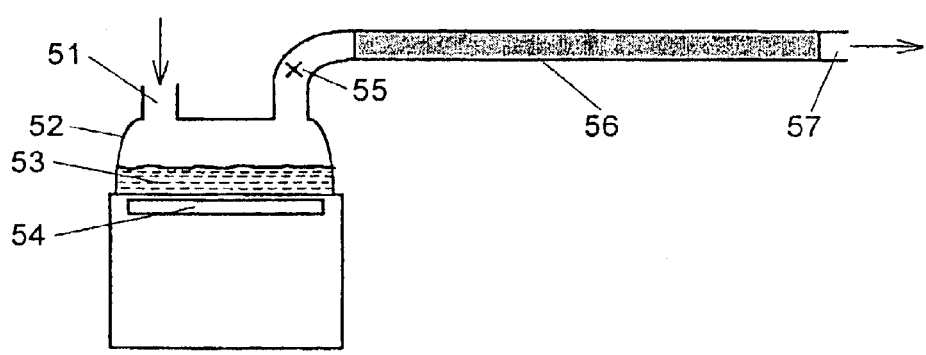
FIG. 11 shows a humidifier configuration using the tube in FIG. 10.

The PTC tube described in FIG. 10 allows us to create a humidifier which doesn't use any sensor at the patient airway. FIG. 11 shows a humidifier configuration using this tube. Gas enters humidification chamber 52 via inlet port 51 and is humidified by water 53, heated by heater plate 54. Absolute humidity sensor 55 controls the heater plate so that the gas passing sensor 55 is at a desired level of absolute humidity. PTC tube 56 is heated by an external voltage (not shown) so that the internal surface temperature is at a constant desired temperature, which is selected to be above the dewpoint of the gas. The gas which leaves tube 56 at outlet 57 will therefore be near the temperature of the tube, and containing the desired level of absolute humidity which was controlled by absolute humidity sensor 55.

A variation of the system shown in FIG. 11 would be to use a temperature sensor at position 55. Another variation of a tube with a constant internal wall temperature would a delivery tube with heated water or other fluid pumped through smaller conduits in the wall of the delivery tube. Since the heated fluid has a high specific heat relative to air, the temperature of the fluid remains fairly constant during passage through the delivery wall conduits.

Use of a Sensor/Heater Manifold

Traditional humidifiers have tended to use sensors that are probe shaped, so that they can be inserted through specifically designed holes in the side of the breathing circuit to measure temperature. However the humidifier configurations that have been described in this patent incorporate many sensors around the chamber, so the use of a manifold 59 as shown in FIG. 12 may be useful.

Figure 12:
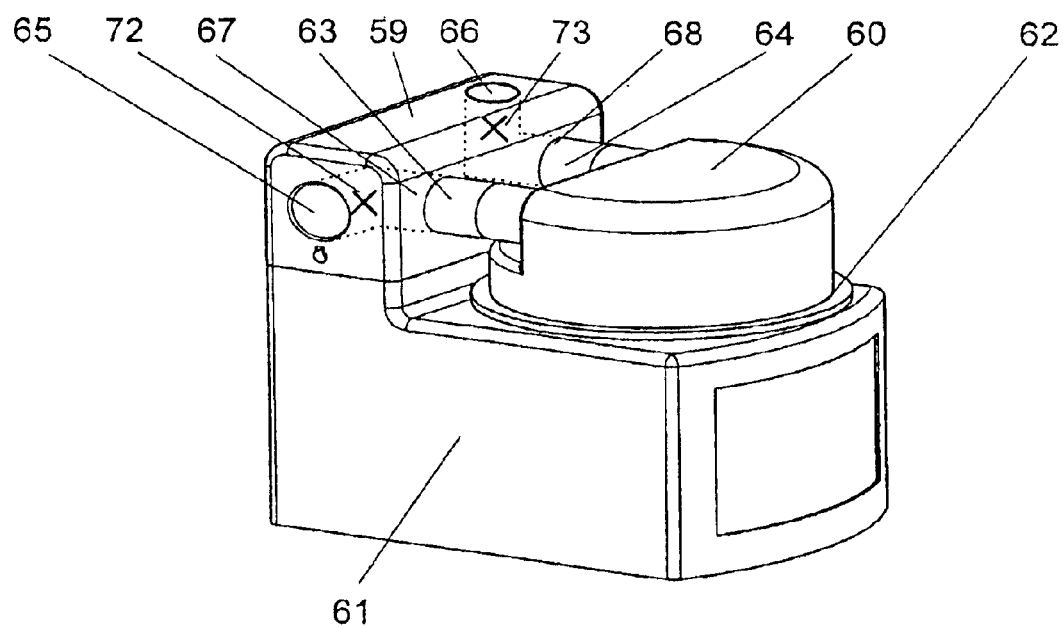
FIG. 12 shows the chamber manifold.
Figure 13:
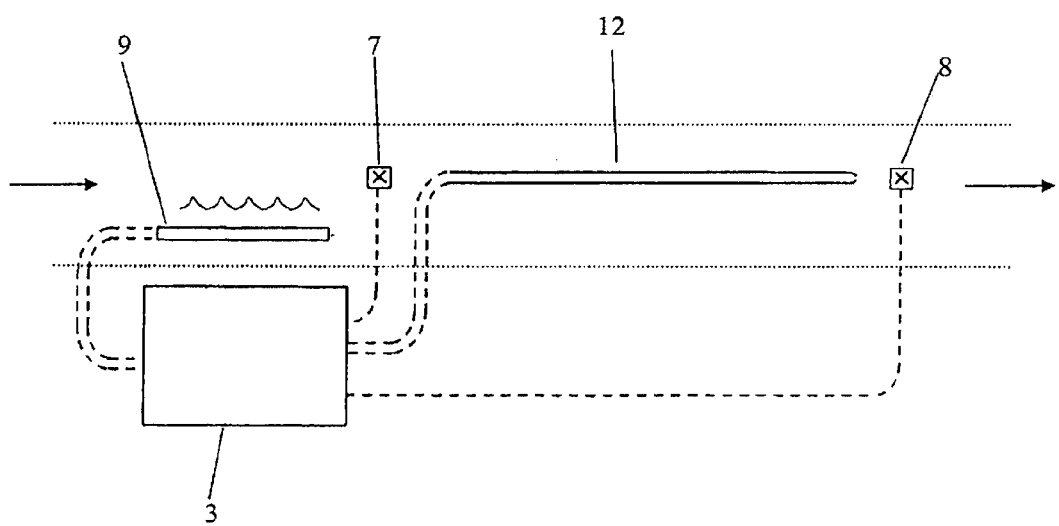
FIG. 13 is a block of the controller functions relating to FIG. 1.

The humidification chamber 60 is a removable item which can be slid onto the humidifier base 61 as shown in FIG. 12. As the chamber 60 is slid onto the humidifier base 61, its base makes contact with heater plate 62 and its inlet and outlet ports 63 and 64 make contact with holes 67 and 68 inside the manifold 59. Dry air to be humidified enters the manifold at port 65, passes out of the manifold through port 67, and flows through port 63 into the chamber 60, where it is humidified.

After leaving chamber 60 the humid gas passes through chamber port 64 into manifold port 68. Finally the humid gas leaves manifold 59 through port 66 and passes to the breathing circuit.

The manifold may be a separate, removable assembly, or it may be an integral part of the humidifier base. It may contain temperature sensors, humidity sensors, flow sensors, or a heater element. These would be located inside the manifold 59 at positions 72 and 73. The manifold 59 may be heated to prevent condensation of humid gas. It could connect to both chamber ports 63 and 64 as described, or it may only connect to the outlet port 64. One advantage of using a manifold is that many sensors or heaters can be combined in a single, cleanable assembly, rather than requiring separate probes which need to be plugged into the breathing circuit. This simplifies connection and setup for the user. Another advantage of a manifold is that the incoming dry gas temperature and flow rate can easily be measured without additional probes and connections.

Variations on the Described Configurations

Although absolute humidity sensors have been described with all of the different humidification schemes described in this patent, relative humidity sensors could also be used. This may involve slightly different control algorithms to the ones described in this patent. Alternatively, a relative humidity sensor could be combined with a temperature sensor. This allows the absolute humidity to be calculated from relative humidity and temperature, rather than being measured directly.

All of the novel humidification schemes that have been described in this patent could be used with additional temperature sensors. These may provide additional benefits such as providing a safety backup in the event of a failed humidity sensor. Another benefit would be maintaining the temperature being delivered to the patient within certain limits so that the relative humidity is not too low, even though the absolute humidity was acceptable.

Similarly it may be useful to measure the air flow rate through the humidifier, as this is an important parameter which affects humidifier control. Therefore flow sensors could be incorporated within any of the previously described systems. One useful prior art flow sensor construction would be to use a sensor based on heat loss from a hot element in the airstream. If a heated humidity sensor is used, the amount of heating that is required for the sensor to achieve temperature can be used to determine the gas flow rate.

Infection control is a prime consideration when designing medical components. To prevent bacterial colonisation of the components in the humidification system, any parts which come in contact with the gas stream could be made out of antibacterial plastic. To prevent contamination of sensor probes, the probe ports could incorporate a disposable sheath which protects the probe from pathogens in the breathing circuit. This would be particularly applicable to temperature probes. In general humidity probes need to have contact with the gas stream so a disposable sheath would be inapplicable to humidity sensors, unless they worked on optical principles, or unless the sheath was made of water vapour permeable material, which did not allow the passage of pathogens. The protective sheath could be an integral part of a disposable breathing circuit.

What we claim is:

1. A humidification apparatus for humidifying a gases flow to be supplied to a patient or other person in need of such gases comprising:
   humidification chamber and having an inlet and an outlet to allow said gases flow to pass through said humidification chamber,
   a chamber heater provided adjacent said humidification chamber and adapted to vaporise liquid water in said humidification chamber in order to provide water vapour to said gases flow passing through said humidification chamber,
   a conduit connected to said outlet of said humidification chamber to convey said gases flow to said patient or other person in need of such gases, and
   humidity sensor configured to provide an indication of the absolute humidity of said gases flow at least at one of said humidification chamber and at a point along said conduit in said gases flow,
   a controller or processor configured or programmed to receive as inputs said indication of the absolute humidity of said gases flow, estimate a rate of condensation of said gases in said conduit based on said inputs and control said chamber heater based on said rate of condensation to minimise condensation of said gases in said conduit.

2. A humidification apparatus as claimed in claim 1 wherein said conduit includes a conduit heater to heat said gases flow, and said controller or processor is configured to control said conduit heater based on said rate of condensation to minimise condensation of said gases in said conduit.

3. A humidification apparatus as claimed in claim 2 wherein said humidity sensor including a first absolute humidity sensor in substantial proximity to said outlet of said humidification chamber.

4. A humidification apparatus as claimed in claim 3 wherein said conduit having a patient end, distal to said end connected to said outlet of said humidification chamber, and said humidity sensor further comprising a second absolute humidity sensor in substantial proximity to said patient end of said conduit.

5. A humidification apparatus as claimed in claim 4 wherein said estimate of the rate of condensation is based on the difference between the absolute humidity at said outlet of said humidification chamber, as indicated by the output of said first absolute humidity sensor, and the absolute humidity at said patient end of said conduit, as indicated by the output of said second absolute humidity sensor.

6. A humidification apparatus as claimed in claim 5 wherein said controller or processor is configured to:
   i) energise said conduit heater depending on at least said estimate of the rate of condensation, to a level appropriate to substantially vaporise any liquid condensate present in said conduit; and
   ii) energise said conduit heater depending on at least said estimate of the rate of condensation, to a level appropriate to minimise any condensation of the vapour from said gases in said conduit.

7. A humidification apparatus as claimed in claim 6 wherein said steps (i) and (ii) are repeated continually at regular intervals.

8. A humidification apparatus as claimed in claim 6 wherein said steps (i) and (ii) are alternated at regular intervals.

9. A humidification apparatus as claimed in claim 2 wherein said conduit having a patient end, distal to said end connected to said outlet of said humidification chamber and said apparatus further comprising a first temperature sensor in substantial proximity to said outlet of said humidification chamber and an absolute humidity sensor in substantial proximity to said patient end of said conduit.

10. A humidification apparatus as claimed in claim 2 further comprising at least a temperature sensor and at least one relative humidity sensor providing an indication of the temperature and relative humidity at least at one point in the flow path of said gases flow through said apparatus.

11. A humidification apparatus as claimed in claim 2 wherein further comprising flow sensing means adapted to provide an indication of the rate of flow of said gases flown through said apparatus.

12. A humidification apparatus as claimed in claim 11 wherein said flow sensing means comprising a heated element adapted to maintain a substantially constant temperature and being provided in the flow path of said gases through said apparatus, the heat loss therefrom providing an indication of the rate of flow of said gases.

13. A humidification apparatus as claimed in claims 1 or 2 wherein said humidity sensor further comprising a disposable cover providing a substantial barrier to microorganisms between said flow of gases and said humidity sensor.

14. A humidification apparatus as claimed in claims 1 or 2 wherein said humidity sensor further comprising porous disposable cover means for providing porous material as a substantial barrier to microorganisms between said flow of gases and said absolute humidity sensor.

15. A humidification apparatus as claimed in claim 9 further comprising a conduit heater adapted to heat said gases flow in said conduit and/or said conduit, and said controller or processor configured to energise said conduit heater depending on at least said estimate of the rate of condensation, at a level appropriate to minimise any condensation of the vapour from said gases in said conduit as well as convey said gases flow to said patient or other person in need of such gases substantially at a predetermined level of absolute humidity.

16. A humidification apparatus for humidifying a gases flow to be supplied to a patient or other person in need of such gases comprising:
    a humidification chamber and having an inlet and an outlet to allow said gases flow to pass through said humidification chamber,
    chamber heater provided adjacent said humidification chamber including wet heating means adapted to vaporise liquid water in said humidification chamber in order to provide water vapour to said gases flow passing through said humidification chamber and dry heating means adapted to directly heat said gases flow passing through said humidification chamber,
    a conduit connected to said outlet of said humidification chamber to convey said gases flow to said patient or other person in need of such gases, including insulation to minimise the rate of heat energy lost by said gases flow in said conduit,
    a controller configured to energise said wet heating means and said dry heating means to achieve a desired level of absolute humidity and to minimise the condensation of the vapour from said gases in said conduit.

17. A humidification apparatus for humidifying a gases flow to be supplied to a patient or other person in need of such gases comprising:
    a humidification chamber and having an inlet and an outlet to allow said gases flow to pass through said humidification chamber,
    chamber heater provided adjacent said humidification chamber adapted to vaporise liquid water in said humidification chamber in order to provide water vapour to said gases flow passing through said humidification chamber,
    a conduit connected to said outlet of said humidification chamber to convey said gases flow to said patient or other person in need of such gases, and
    a regulated conduit heater adapted to regulate the temperature profile of said gases flow along said conduit and/or of said conduit, to substantially coincide with a predetermined profile, wherein said regulated conduit heater comprising at least one section of negative temperature coefficient material wherein the localised electrical resistance of said section is negatively related to the localised temperature.

18. A humidification apparatus for humidifying a gases flow to be supplied to a patient or other person in need of such gases comprising:
    a humidification chamber and having an inlet and an outlet to allow said eases flow to pass through said humidification chamber,
    chamber heater provided adjacent said humidification chamber adapted to vaporise liquid water in said humidification chamber in order to provide water vapour to said gases flow passing through said humidification chamber,
    a conduit connected to said outlet of said humidification chamber to convey said gases flow to said patient or other person in need of such gases, and
    a regulated conduit heater adapted to regulate the temperature profile of said gases flow along said conduit and/or of said conduit, to substantially coincide with a predetermined profile wherein said regulated conduit heater comprising a plurality of sections of positive temperature coefficient material wherein the localised electrical resistance of each said section is positively related to the localised temperature section and at least two electrical conductors running along said conduit, each said conductor being electrically connected to a separate portion of each said section and each said section being electrically isolated from all other sections except for the connection through each said conductor.

19. A humidification apparatus for humidifying a gases flow to be supplied to a patient or other person in need of such gases comprising:
    a humidification chamber having an inlet and an outlet to allow said gases flow to pass through said humidification chamber,
    chamber heater provided adjacent said humidification chamber adapted to vaporise liquid water in said humidification chamber in order to provide water vapour to said gases flow passing through said humidification chamber,
    a conduit connected to said outlet of said humidification chamber to convey said gases flow to said patient or other person in need of such gases, and
    a regulated conduit heater adapted to regulate the temperature profile of said gases flow along said conduit and/or of said conduit, to substantially coincide with a predetermined profile wherein said conduit further comprising an inspiratory conduit in fluid communication with said outlet of said humidification chamber, a connector means in fluid communication with said inspiratory conduit, a flexible tube extension in fluid communication with said connector and a patient interface in fluid communication with said flexible tube extension adapted to convey said gases flow to said patient.

20. A humidification apparatus as claimed in claim 19 wherein said flexible tube extension including a flexible tube extension heater with at least one section of positive temperature coefficient material wherein the localised electrical resistance of said material is positively related to the localised temperature.

21. A humidification apparatus as claimed in claims 19 or 20 wherein said patient interface comprising a patient interface heater including at least one section of positive temperature coefficient material wherein the localised electrical resistance of each said section of said material is positively related to the localised temperature.

22. A humidification apparatus for humidifying a gases flow to be supplied to a patient or other person in need of such gases comprising:

a humidification chamber having an inlet and an outlet to allow said gases flow to pass through said humidification chamber, chamber heater provided adjacent said humidification chamber adapted to vaporise liquid water in said humidification chamber in order to provide water vapour to said gases flow passing through said humidification chamber, a conduit connected to said outlet of said humidification chamber to convey said gases flow to said patient or other person in need of such gases, and a regulated conduit heater adapted to regulate the temperature profile of said gases flow along said conduit and/or of said conduit, to substantially coincide with a predetermined profile further comprising a humidity sensor for providing an indication of the absolute humidity of said gases flow at said outlet of said humidity chamber.

23. A humidification apparatus as claimed in claim 22 wherein further comprising a temperature sensor for providing an indication of the temperature of said gases flow at said outlet of said humidification chamber.

24. A humidification apparatus for humidifying a gases flow to be supplied to a patient or other person in need of such gases comprising:

a humidification chamber having an inlet and an outlet to allow said gases flow to pass through said humidification chamber, chamber heater provided adjacent said humidification chamber adapted to vaporise liquid water in said humidification chamber in order to provide water vapour to said gases flow passing through said humidification chamber, a conduit connected to said outlet of said humidification chamber to convey said gases flow to said patient or other person in need of such gases, and a regulated conduit heater adapted to regulate the temperature profile of said gases flow along said conduit and/or of said conduit, to substantially coincide with a predetermined profile wherein said conduit comprising a double walled inspiratory conduit and said regulated conduit heater comprising the provision of warm fluid circulated between the inner wall and outer wall of said double walled inspiratory conduit.

25. A humidification apparatus for humidifying a gases flow to be supplied to a patient or other person in need of such gases comprising:

a humidification chamber having an inlet and an outlet to allow said gases flow to pass through said humidification chamber, chamber heater provided adjacent said humidification chamber adapted to vaporise liquid water in said humidification chamber in order to provide water vapour to said gases flow passing through said humidification chamber, a conduit connected to said outlet of said humidification chamber to convey said gases flow to said patient or other person in need of such gases, and a regulated conduit heater adapted to regulate the temperature profile of said gases flow along said conduit and/or of said conduit, to substantially coincide with a predetermined profile wherein said predetermined profile relates to a substantially constant temperature along the length of said conduit.

26. A method for humidifying a gases flow to be supplied to a patient or other person in need of such gases comprising:

transferring water vapour or humidity to gases passing through a chamber, conveying said gases flow to said patient or other person in need of such gases from said chamber, and sensing the absolute humidity of said gases flow at one point along its flow path, estimating a rate of condensation of said gases based on said absolute humidity and controlling the transferred humidity based on said rate of condensation to minimise condensation of said gases.

27. A method as claimed in claim 26 further comprising the step of heating said gases flow at least at one point along its flow path, and controlling the transferred heat based on said rate of condensation to minimise condensation of said gases.

28. A method as claimed in claim 27 wherein said absolute humidity is sensed in substantial proximity to said chamber.

29. A method as claimed in claim 28 wherein said absolute humidity is also sensed in substantial proximity to a patient.

30. A method as claimed in claim 29 wherein said estimate of the rate of condensation is based on the difference between the absolute humidity at said outlet of said chamber, and the absolute humidity at said patient.

31. A method as claimed in claim 30 further comprising the steps of:

i) heating said gases flow depending on at least said estimate of the rate of condensation, to a level appropriate to substantially vaporise any liquid condensate; and ii) heating said gases flow depending on at least said estimate of the rate of condensation, to a level appropriate to minimise any condensation of the vapour from said gases.

32. A method as claimed in claim 31 said steps (i) and (ii) are repeated continually at regular intervals.

33. A method as claimed in claim 31 wherein said steps (i) and (ii) are alternated at regular intervals.

34. A method as claimed in claim 27 wherein the temperature of said gases is sensed in substantial proximity to the outlet of said chamber and the absolute humidity is sensed in substantial proximity to said patient.

35. A method as claimed in claim 34 further comprising the steps of heating said gases, and controlling the transferred heat depending on at least said estimate of the rate of condensation, at a level appropriate to minimise any condensation of the vapour from said gases as well as convey said gases flow to said patient or other person in need of such gases substantially at a predetermined level of absolute humidity.

36. A method as claimed in claim 27 wherein the temperature and relative humidity at least at one point in the flow path of said gases flow is sensed.

37. A humidification apparatus for humidifying a gases flow to be supplied to a patient or other person in need of such gases comprising:
- a humidification chamber and having an inlet and an outlet to allow said gases flow to pass through said humidification chamber,
- a chamber heater provided adjacent said humidification chamber and adapted to vaporise liquid water in said humidification chamber in order to provide water vapour to said gases flow passing through said humidification chamber,
- a conduit connected to said outlet of said humidification chamber to convey said gases flow to said patient or other person in need of such gases, and
- a humidity sensor configured to provide an indication of the absolute humidity of said gases proximate said outlet,
- a controller or processor configured or programmed to receive as inputs said indication of the absolute humidity of said gases flow, and energise said chamber heater based on said absolute humidity to achieve a predetermined absolute humidity at said outlet, and configured or programmed to vary said predetermined absolute humidity to substantially avoid condensation in said conduit.

* * * * *

UNITED STATES PATENT AND TRADEMARK OFFICE
CERTIFICATE OF CORRECTION

PATENT NO. : 6,918,389 B2
DATED : July 19, 2005
INVENTOR(S) : Paul John Seakins, Malcom David Smith and Mohammad Thudor It is certified that error appears in the above-identified patent and that said Letters Patent is hereby corrected as shown below:

Column 3,
Line 52, "is a block of" should be -- is a block diagram of --.

Column 4,
Line 33, "port S" should be -- port 5 --.

Column 6,
Line 55, "Snow rates." should be -- flow rates. --.

Column 10,
Line 12, "humidification" should be -- a humidification --.

Column 11,
Line 33, "in claim 9" should be -- in claim 1 --.

Column 13,
Line 40, "humidity chamber" should be -- humidification chamber --.
Line 42, "wherein further" should be -- further --.

Signed and Sealed this

Twentieth Day of September, 2005

JON W. DUDAS
*Director of the United States Patent and Trademark Office*